(12) United States Patent
Bertoch et al.

(10) Patent No.: US 6,755,191 B2
(45) Date of Patent: Jun. 29, 2004

(54) SECURING DEVICE FOR AN ENDOTRACHEAL TUBE

(75) Inventors: Todd M. Bertoch, APO (AP); Ted F. Gingrich, San Antonio, TX (US); Steven C. Walker, Baldwin, MO (US); John M. Shepherd, San Antonio, TX (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/789,708

(22) Filed: Feb. 22, 2001

(65) Prior Publication Data

US 2002/0092526 A1 Jul. 18, 2002

Related U.S. Application Data

(60) Provisional application No. 60/183,772, filed on Feb. 22, 2000.

(51) Int. Cl.[7] .............................................. A61M 16/00
(52) U.S. Cl. ............................. 128/200.26; 128/207.14; 128/DIG. 26
(58) Field of Search ....................... 128/200.26, 207.14, 128/207.15, 207.12, DIG. 26

(56) References Cited

U.S. PATENT DOCUMENTS

| | | | |
|---|---|---|---|
| 2,521,084 A | 9/1950 | Oberto | |
| 2,669,988 A | 2/1954 | Carpenter | |
| 2,693,182 A | * 11/1954 | Phillips | 128/207.17 |
| 2,820,457 A | * 1/1958 | Phillips | 128/207.17 |
| 2,882,893 A | 4/1959 | Godfroy | |
| 2,908,269 A | * 10/1959 | Cheng | 128/207.17 |
| 3,602,227 A | * 8/1971 | Andrew | 128/207.17 |
| 3,760,811 A | * 9/1973 | Andrew | 128/207.17 |
| 3,774,616 A | * 11/1973 | White et al. | 128/200.26 |
| 3,908,665 A | 9/1975 | Moses | |
| 4,112,936 A | 9/1978 | Blachly | |
| 4,198,970 A | 4/1980 | Luomanen | |
| 4,205,819 A | * 6/1980 | Soika | 251/6 |
| 4,222,391 A | 9/1980 | Rawson et al. | |
| 4,270,529 A | * 6/1981 | Muto | 128/200.26 |
| 4,270,531 A | 6/1981 | Blachly, deceased et al. | |
| 4,351,330 A | 9/1982 | Scarberry | |
| 4,351,331 A | * 9/1982 | Gereg | 128/207.17 |
| 4,392,857 A | * 7/1983 | Beran | 604/179 |
| 4,425,911 A | 1/1984 | Luomanen et al. | |
| 4,495,945 A | 1/1985 | Liegner | |
| 4,502,478 A | 3/1985 | Lifton | |

(List continued on next page.)

FOREIGN PATENT DOCUMENTS

WO     WO 01/58349 A1     8/2001

*Primary Examiner*—Aaron J. Lewis
*Assistant Examiner*—Joseph F. Weiss, Jr.
(74) *Attorney, Agent, or Firm*—Elizabeth Arwine

(57) ABSTRACT

A securing device for an endotracheal tube preferably includes a shield having an opening through which the endotracheal tube can pass and a clamp mounted on the shield for holding the endotracheal tube. A bite block for preventing occlusion of the endotracheal tube by a patient's teeth may be mounted on an opposite surface of the shield from the clamp.

18 Claims, 2 Drawing Sheets

U.S. PATENT DOCUMENTS

| | | | |
|---|---|---|---|
| 4,530,354 A | * 7/1985 | Froilan | 128/207.17 |
| 4,640,273 A | 2/1987 | Greene et al. | |
| 4,676,240 A | 6/1987 | Gardy | |
| 4,683,882 A | * 8/1987 | Laird | 128/207.17 |
| 4,699,616 A | 10/1987 | Nowak et al. | |
| 4,744,358 A | 5/1988 | McGinnis | |
| 4,774,944 A | * 10/1988 | Mischinski | 128/207.17 |
| 4,791,941 A | 12/1988 | Schaefer | |
| 4,944,313 A | 7/1990 | Katz et al. | |
| 5,026,352 A | 6/1991 | Anderson | |
| 5,069,206 A | * 12/1991 | Crosbie | 128/207.17 |
| 5,123,410 A | 6/1992 | Greene et al. | |
| 5,174,284 A | 12/1992 | Jackson | |
| 5,193,544 A | 3/1993 | Jaffe | |
| 5,205,281 A | 4/1993 | Buchanan | |
| 5,282,464 A | 2/1994 | Brain | |
| 5,305,742 A | * 4/1994 | Styers et al. | 128/207.17 |
| 5,318,017 A | 6/1994 | Ellison | |
| 5,320,097 A | * 6/1994 | Clemens et al. | 128/207.17 |
| 5,355,874 A | 10/1994 | Bertram | |
| 5,402,776 A | * 4/1995 | Islava | 128/207.17 |
| 5,413,095 A | 5/1995 | Weaver | |
| 5,501,216 A | * 3/1996 | Byrd | 128/207.17 |
| 5,529,062 A | * 6/1996 | Byrd | 128/207.17 |
| 5,551,421 A | * 9/1996 | Noureldin et al. | 128/207.17 |
| 5,626,128 A | * 5/1997 | Bradley et al. | 128/200.26 |
| 5,655,519 A | 8/1997 | Alfery | |
| 5,715,816 A | 2/1998 | Mainiero et al. | |
| 5,746,202 A | 5/1998 | Pagan | |
| 5,782,236 A | 7/1998 | Ess | |
| 5,803,079 A | 9/1998 | Rogers et al. | |
| 5,806,516 A | * 9/1998 | Beattie | 128/207.17 |
| 5,829,430 A | 11/1998 | Islava | |
| 5,894,840 A | * 4/1999 | King | 128/200.26 |
| 6,244,865 B1 | 6/2001 | Nelson et al. | |
| 2002/0095118 A1 | 7/2002 | Bertoch et al. | |
| 2002/0095119 A1 | 7/2002 | Bertoch et al. | |

* cited by examiner

SECURING DEVICE FOR AN ENDOTRACHEAL TUBE

This application claims the benefit of U.S. provisional Application Serial No. 60/183,772, filed Feb. 22, 2000, which is hereby incorporated by reference.

FIELD OF THE INVENTION

This invention relates to a device for securing an endotracheal tube with respect to a patient's mouth while preventing occlusion of the endotracheal tube by the patient.

BACKGROUND OF THE INVENTION

Catheters are employed for many purposes to provide for passage of fluids, including gases, to and from the human body. One type of catheter is an endotracheal tube, which is adapted to be inserted through the oral cavity of a patient and into the trachea to provide for the supply of fluids to the body, for the monitoring of internal conditions in the body and to provide for removal of secretions from within the body.

It is desirable to secure the endotracheal tube in place within the patient to prevent it from being inadvertently mainstem intubated (advanced into the patient) or extubated (retracted (or removed) from the patient's mouth) after it has been properly positioned; however, it is difficult to properly secure an endotracheal tube to a patient's face to prevent these events. Neck straps are effective for holding endotracheal tubes, but the neck straps can often hinder jugular venous flow or impede line placement within the patient. Tapes and adhesives are ineffective routinely, because of the presence of facial hair, dirt, blood, debris, perspiration, excessive soft tissue or facial trauma.

Another problem is that the endotracheal tube is usually relatively easy to deform and passes between the patient's teeth if inserted orally, it is desirable to prevent the lumen of the endotracheal tube from being occluded by a patient's teeth when the patient attempts to bite down. Occlusion of the endotracheal tube can lead to, for example, hypoxia, hypercarabia, a negative pressure pulmonary edema, or other similar conditions. The various discussed restraining approaches are ineffective in protecting against possible occlusion of the endotracheal tube. Bite blocks can be effective in keeping a patient's jaw open and thus prevent the teeth from clamping down on the endotracheal tube. The problem is that the bite block is yet another piece of equipment that may be inserted into the patient's mouth along with other medical apparatuses including, for example, multiple hoses/tubes and pulse oximeter sensors.

Notwithstanding the present methods and ways, a need still exists for a better way to secure an endotracheal tube in a patient while avoiding the above-discussed problems.

SUMMARY OF THE INVENTION

The present invention preferably provides a securing device for an endotracheal tube that can secure the endotracheal tube to a patient but at the same time permits the position of the endotracheal tube with respect to the patient to be readily adjusted by a medical professional.

The present invention also preferably provides a securing device that prevents occlusion of an endotracheal tube by a patient's teeth.

According to one aspect of the present invention, a securing device for an endotracheal tube preferably includes a shield for installation on an exterior of a patient's mouth and a clamp mounted on the shield. The shield preferably has an opening through which the endotracheal tube passes. The clamp preferably has an open position, which permits the position of the endotracheal tube passing through the shield opening to be adjusted, and a closed position, which immobilizes the endotracheal tube passing through the shield opening without occluding the endotracheal tube. The securing device may also include a bite block for insertion between a patient's teeth to prevent occlusion of the endotracheal tube passing through the opening in the shield by a patient's teeth.

A securing device according to the present invention may be used with any type of endotracheal tube, which needs to be inserted into a patient's airway via the mouth, such as a respiratory tube, a laryngeal mask, or when a Combitube intubation occurs. The securing device can be used in any setting in which it is desired to secure the endotracheal tube, such as in an operating room, an intensive care unit, or in the field.

An objective of the invention is to maintain an endotracheal tube at a constant depth within the patient.

Another objective of the invention is to prevent an endotracheal tube from being occluded by the patient's teeth.

Another objective of the invention is to take up as little mouth space to allow for the insertion of additional medical instruments as may be found to be necessary by the treating medical professional(s).

Another objective of the invention is to provide a device that is easy to use for medical professionals.

A further objective of the invention is to provide a device that can be used in the operating room, the intensive care unit (ICU), the emergency room, or the field in any situation that requires a quick, easy, and reliable means of securing an endotracheal tube or a catheter inserted in the patient's mouth.

An advantage of the invention is that it securely holds an endotracheal tube at a constant depth within the patient once set.

Another advantage of the invention is the prevention of occlusion of an inserted endotracheal tube in a patient.

Another advantage of the invention is that it is easy to use during the initial insertion of an endotracheal tube, any adjustment of the depth within the patient of the endotracheal tube, and the removal of the endotracheal tube.

Another advantage of the invention is that it leaves space for the insertion of additional medical instruments into the patient's mouth and/or nose.

Another advantage of the invention is that it can still work when debris, blood, facial hair, dirt, perspiration, excessive soft tissue and facial trauma are present in the vicinity and even within the oral cavity.

A further advantage of the invention is that an endotracheal tube is protected from occlusion resulting from forces being applied to it by the patient's jaw and teeth.

A further advantage of the invention is the minimization and elimination of the likelihood of inadvertent extubation or mainstem intubation.

Further features and advantages of the present invention, as well as the structure and operation of various embodiments of the present invention, are described in detail below with reference to the accompanying drawings. Given the following enabling description of the drawings, the apparatus and the method should become evident to a person of ordinary skill in the art.

BRIEF DESCRIPTION OF THE DRAWINGS

The use of cross-hatching within these drawings should not be interpreted as a limitation on the potential materials

FIG. 2 also illustrates an alternative embodiment of the invention.

DETAILED DESCRIPTION OF THE PREFERRED EMBODIMENTS

Figure 1:
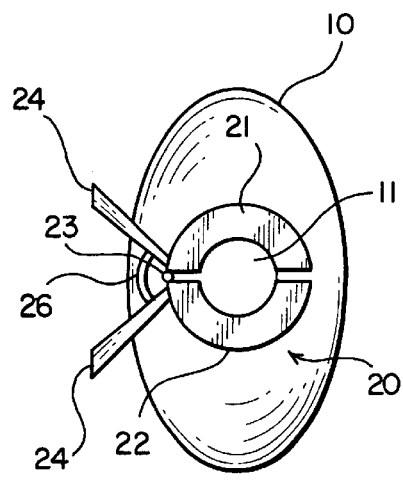
FIG. 1 illustrates a front view of a preferred embodiment of a securing device according to the present invention with a clamp of the securing device in a closed position.
Figure 2:
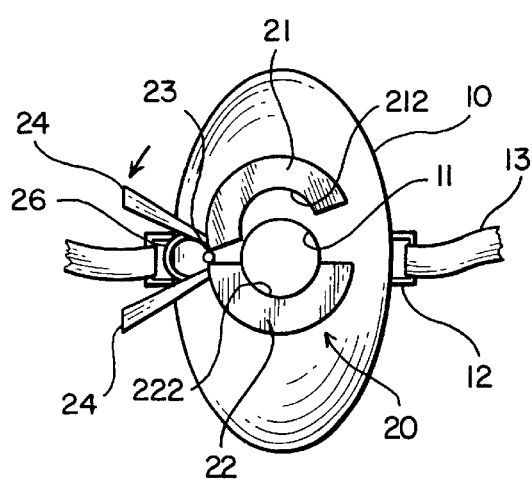
FIG. 2 depicts a front view of the embodiment of FIG. 1 with the clamp in an open position.
Figure 3:
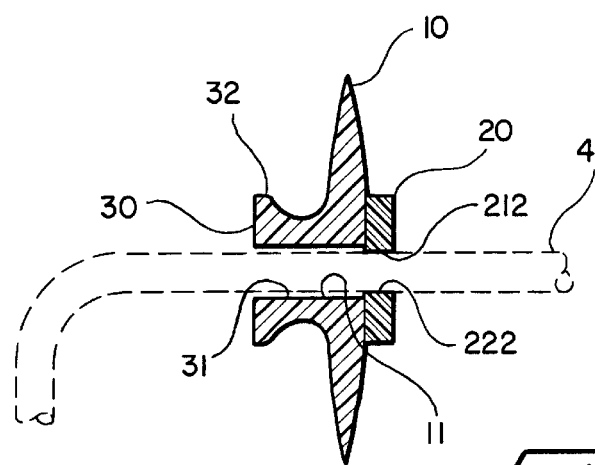
FIG. 3 illustrates a side cross-section view of the embodiment of FIG. 1.
Figure 4:
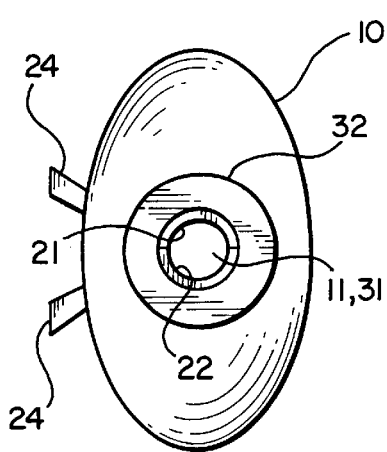
FIG. 4 depicts a rear view of the embodiment of FIG. 1.

FIGS. 1–4 illustrate a preferred embodiment of a securing device according to the present invention. The illustrated embodiment is intended for use with an endotracheal tube, more specifically it may be employed with respiratory tubes.

The illustrated securing device preferably includes a shield 10 positioned on an exterior of a patient's mouth. The shield 10 preferably has an opening 11 for receiving an endotracheal tube 40 such as a respiratory tube (shown in phantom in FIG. 3). The securing device also preferably includes a clamp 20 (preferably a spring-loaded C-clamp) mounted on one side of the shield 10 for releasably restraining the endotracheal tube 40 with respect to the shield 10. The securing device may also include a bite block 30 disposed on the opposite side of the shield 10 from the clamp 20 for protecting the endotracheal tube 40 passing through the securing device from occlusion by a patient's teeth.

The shield 10 can be any member having outer dimensions large enough to prevent the shield 10 from readily entering a patient's mouth. Thus, preventing the endotracheal tube 40 to which the shield 10 is attached from being inadvertently advanced into a patient's mouth after it has been properly positioned in the patient's airway. The shape of the shield 10 is not critical. The shield 10 preferably is a plate-like member with a thickness that is small relative to its height and width. The shield 10 preferably has an oblong shape with a height that is larger than the height of the opening defined by a patient's lips when the mouth is wide open. Preferably, the shield 10 has a width that is smaller than its height to enable tubes other than the endotracheal tube 40 (such as oral gastric tubes, an esophageal stethoscope, or pulse oximeter sensors) to be inserted into the sides of a patient's mouth adjoining the widthwise sides of the shield 10.

An opening 11 for receiving the endotracheal tube 40 is formed through the thickness of the shield 10. The opening 11 preferably has a diameter that is sufficiently large that the endotracheal tube 40 can easily pass through it. More preferably, the opening 11 allows the position of the endotracheal tube 40 with respect to the shield 10 to be adjusted without the exertion of much force. For example, the endotracheal tube 40 may fit loosely inside the opening 11.

The clamp 20 preferably is used to releasably secure the endotracheal tube 40 to the shield 10. The clamp 20 preferably has a closed position, shown in FIG. 1, and an open position, shown in FIG. 2. Preferably when the clamp 20 is open, the attached endotracheal tube 40 can freely move in its longitudinal direction with respect to the shield 10 to enable the depth in the patient of the endotracheal tube 40 to be adjusted. Preferably when the clamp 20 is closed, the clamp 20 engages the endotracheal tube 40 sufficiently tight to resist movement of the endotracheal tube 40 in its longitudinal direction with respect to the shield 10 without occluding the endotracheal tube 40. This function of the clamp 20 can be accomplished by a variety of structures.

The clamp 20 preferably includes first and second jaws 21, 22 pivotally connected to each other at a pivot point 23 and biased towards the closed position of the clamp 20 by a spring 26. The clamp 20 preferably is opened against the force of the spring 26 by squeezing the two levers (or handles) 24 towards each other, each of the levers 24 preferably being connected to one of the jaws 21, 22. Alternatively, the levers 24 and jaws 21, 22 may have a scissor arrangement that includes an elastic/spring force mechanism (such as a rubber band or a spring) to hold the levers 24 together with a force is desirable to be included.

When the clamp 20 is in the closed position, the two jaws 21, 22 preferably define an opening sized to enable the jaws 21, 22 to frictionally engage the outer surface of the endotracheal tube 40 without occluding the endotracheal tube 40. The radial inner surfaces 212, 222 of the jaws 21, 22, which contact the outer surface of the endotracheal tube 40, may be formed so as to have a high coefficient of friction with respect to the outer surface of the endotracheal tube 40. For example, they may be formed of or lined with a material having a high coefficient of friction with respect to the endotracheal tube 40 (such as rubber). Another example is that the radial inner surfaces 212, 222 of the jaws 21, 22 may be formed with protuberances, bumps, ridges, grooves, or other surface irregularities to improve their grip with respect to the endotracheal tube 40.

The jaws 21, 22 may both be movable with respect to the shield 10, or one of the jaws may be immobilized and the other movable to open and close the clamp 20. In the illustrated embodiment, the second (or lower) jaw 22 is maintained stationary with respect to the shield 10, while the first jaw 21 is movable. In the figures, the securing device is positioned with the movable jaw (the first jaw 21) above the stationary jaw (the second jaw 22), but the positions of the jaws 21, 22 may be reversed.

The clamp 20 is not restricted to one having pivotable jaws. For example, it may have jaws that translate rather than rotate with respect to each other to open and close the clamp 20. Alternatively, the clamp 20 may be replaced with a balloon structure.

The bite block 30 can be any member which can prevent the patient from occluding the endotracheal tube 40 passing through the shield 10 by biting the endotracheal tube 40. Since the patient's teeth will typically be able to exert a force on the endotracheal tube 40 only in a limited direction, the bite block 30 need not extend around the entire periphery of the endotracheal tube 40. However, from the standpoints of ease of manufacture and strength, it is frequently convenient if the bite block 30 is a tubular member that completely surrounds the endotracheal tube 40. The illustrated bite block 30 is a body of revolution having a straight longitudinal bore 31 at its axial center which is aligned with the opening 11 in the shield 10. The distal end of the bite block 30 may have an enlarged portion such as an annular flange 32 to help retain the patient's incisors on the bite block 30 between the right side of the flange 32 and the shield 10.

An alternative embodiment of the invention includes a bite block with a flatten bottom surface and flatten top surface to provide rotational stability to the device particularly if there is nothing securing the device to the patient's head. A further alternative structure for the bite block is to have it be two vertical walls with space sufficient between the walls for the inserted endotracheal tube to pass through.

Figure 5:
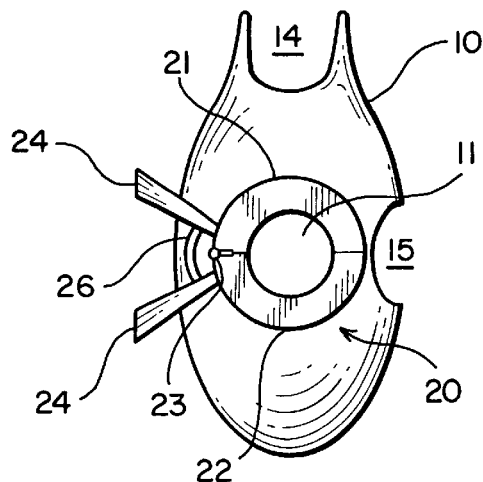
FIG. 5 illustrates an alternative embodiment of the invention.

Another alternative embodiment is for the shield 10 to have a cutout 14 at the top so that the patient's nose will not be covered. A further alternative is for the shield 10 to have one or more cutouts, slots, or holes 15 of sufficient size and shape to allow additional tubes access to the oral cavity as illustrated, for example, in FIG. 5.

Yet another alternative embodiment is to add a structure to the shield 10 such that it can be secured to a patients head. The shield 10 illustrated in FIG. 2 includes a pair of handles (or eyelets) 12 on its opposite widthwise sides, each of which can be connected to an end of a strap 13. The strap 13 preferably is selected from an elastic band, a string, Velcro, rubber, or similar member which preferably passes around the back of the patient's head to hold the shield 10 in position and prevent inadvertent withdrawal of the securing device from the patient's mouth.

Figure 6A:
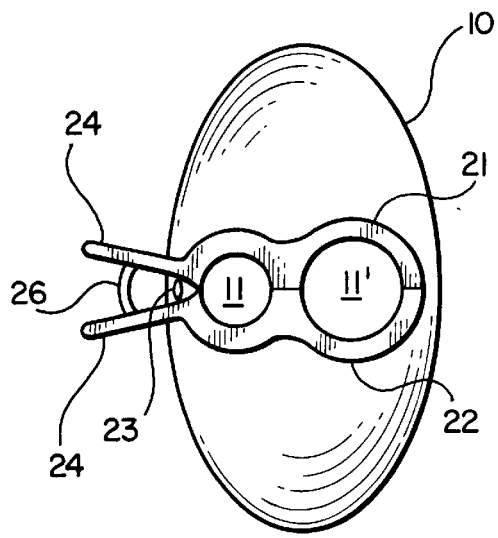
FIGS. 6(a)–(b) depict additional alternative embodiments of the invention.
Figure 6B:
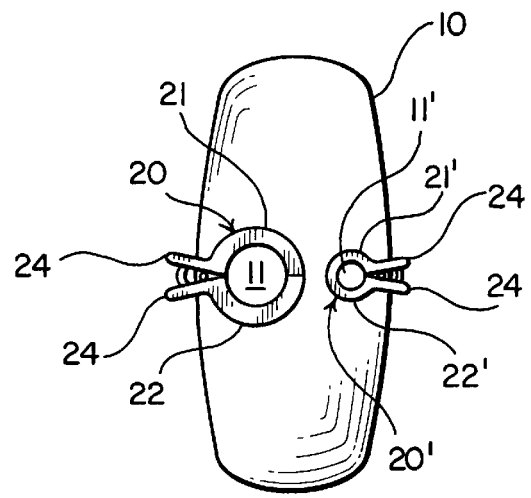

A further alternative embodiment includes an additional clamp to hold a second endotracheal tube as illustrated in FIG. 6(a). This additional clamp may be incorporated into the clamp 20 by providing a second hump to both jaws 21, 22 to form a second opening 11' through the shield 10. Alternatively, the additional clamp may be a separate clamp 20' identical to the clamp 20, but possibly for its inner diameter as illustrated in FIG. 6(b). This separation of the two clamps allows for independent operation of the two clamps. Under either of these two alternative embodiments, the bite block 30 may be of sufficient size to include two bores 31, one each for each respective endotracheal tube inserted through the respective clamp.

The securing device may be made of a variety of materials, including both metals and plastics. It may be convenient if the shield 10 is made of a see-through material, such as a transparent plastic, to enable a patient's mouth and nostrils to be readily observed during use of the securing device to check for obstructions or contamination. The shield 10 and the bite block 30 more preferably are made of at least one of the following: polypropylene, polyvinyl chloride, silicones, epoxies, polyester, thermoplastics, rubber, similar flexible material, etc. More particularly the shield 10 may be made of same material used to manufacture pacifier shields. The different components of the securing device may be separately formed and then secured to each other, or a plurality of the components may be integrally formed with one another.

One possible manufacturing process to build the devices is as follows. In the embodiments illustrated in FIGS. 1–5, the shield 10 and the bite block 30 are integrally formed with one another preferably using a plastic molding process. The jaws 21, 22 are formed separately from the shield 10 and the bite block 30. One way to attach the clamp 20 to the shield 10 is to insert the second jaw 22 into the mold used to form the shield 10 and the bite block 30 so that the shield 10 is partially molded around the second jaw 22. Depending upon the materials of which these components are made, it is also possible to integrally form one of the jaws 21, 22 with the shield 10. Any other desired manner of securing the second jaw 22 to the shield 10 can also be used.

The securing device can be installed on the endotracheal tube 40 either before or after intubation. In one method of using the securing device, prior to intubation, the securing device is slid over one end of the endotracheal tube 40 (such as the distal end) and is positioned on the endotracheal tube 40 adjoining the intraoral region of the tube 40 (the region which is disposed in a patient's mouth during use of the tube 40) or between the intraoral region and the proximal end of the tube 40. The distal end of the endotracheal tube 40 is then inserted into the patient's airway in a conventional manner. As the endotracheal tube 40 is being inserted into the patient's airway, the clamp 20 maintains the securing device at a fixed position on the endotracheal tube 40 where it will not interfere with intubation.

When the distal end has been properly positioned in the patient's airway, the clamp 20 is opened by squeezing the handles 24 towards each other, and the securing device is then slid along the length of the endotracheal tube 40 towards the patient's mouth until the bite block 30 is positioned between the patient's incisors and the shield 10 is at a desired position relative to (such as touching) the patient's lips. The clamp 20 is then allowed to close around the endotracheal tube 40, preventing relative movement of the endotracheal tube 40 and the securing device, and the shield 10 may then be secured to the patient's head with the straps 13 if this structure is present. The endotracheal tube 40 is now immobilized in a desired position with respect to the patient. If it is desired to either insert the endotracheal tube 40 farther into or partially remove from the patient's airway, then the levers 24 on the clamp 20 can be squeezed to release the endotracheal tube 40. When the clamp 20 is open, the position of the endotracheal tube 40 in its longitudinal direction can be adjusted.

A securing device according to the present invention is easy to use because a shield 10, a clamp 20 for resisting movement of a respiratory tube, and a bite block 30 can be combined as one device. The clamp 20 can be operated with a single hand, so one person can readily adjust the securing device. Furthermore, the securing device is not compromised by facial hair, dirt, blood, debris, excessive soft tissue, or facial trauma. It is also more comfortable for a patient than the use of straps, tape, or adhesives to immobilize a respiratory tube with respect to a patient.

Those skilled in the art will appreciate that various adaptations and modifications of the above-described devices and steps can be configured without departing from the scope and spirit of the their use in the method. Therefore, it is to be understood that, within the scope of the appended claims, the method may be practiced and arranged other than as specifically described herein.

What is claimed is:

1. A device for securing a tube to a patient comprising:

a shield including a plate having an opening passing therethrough, and at least one clamp connected to said plate, each of said at least one clamp includes a first jaw movable with respect to said plate between an open position and a closed position, and a second jaw opposing said first jaw, and said second jaw is secured to said shield; and a spring connecting said first jaw and said second jaw, said spring provides a constant compressive force to bias said first jaw towards the closed position.

2. The device as claimed in ciaim 1, wherein said shield is partially molded around said second jaw.

3. The device as claimed in claim 1, wherein said first jaw is pivotable between its first and second positions.

4. The device as claimed in claim 1, further comprising means for securing said shield to the patient.

5. The device as claimed in claim 1, further comprising a bite block mounted on said plate.

6. The device as claimed in claim 5, wherein said bite block is integrally formed with said plate.

7. The device as claimed in claim 5, wherein said lock is mounted on an opposite surface of said plate from said clamp.

8. The device as claimed in claim 7, wherein said bite block includes a passageway passing therethrough and in communication with the opening passing through said plate,
- said first jaw and said second jaw define a space between them, and
- the passageway and the opening are aligned with the space defined by said first jaw and and second jaw.

9. A device for securing a tube inserted in a patient's mouth comprising:
- a shield including a plate having an opening passing therethrough;
- at least one clamp connected to said plate, said clamp includes
  - a first jaw,
  - a second jaw, and
  - a spring connecting said first jaw and said second jaw, said wring provides a constant compressive force to bias said first jaw towards the closed position; and
- a bite block mounted on said plate, said bite block having an opening passing therethrough in communication with the opening of said plate.

10. The device as claimed in claim 9, further comprising a strap, and
- wherein said shield further including a pair of eyelets on opposite edges of said shield, and
- said strap attaches to each of said eyelets.

11. The device as claimed in claim 9, wherein said second jaw is attached to said shield.

12. The device as claimed in claim 9, wherein said bite block includes a flange at the end spaced from said plate.

13. The device as claimed in claim 9, further comprising:
- a second clamp having
  - a first jaw, and
  - a second jaw, and
- wherein said plate having a second opening passing therethrough.

14. A device for securing a tube inserted in a patient's mouth comprisng:
- a shield having an opening passing therethrough,
- at least one clamp connected to said shield,
- a spring, said spring provides a constant compressive force to bias said at least one clamp towards a closed position when said clamp is in the closed position or an open position, and
- a bite block mounted on said shield, said bite block having an opening passing therethrough in communication with the opening of said shield, said bite block includes a flange at the end spaced from said shield; and
- wherein the opening in said shield, one of said at least one clamp, and said bite block are aligned such that an inserted tube passes through each.

15. The device as claimed in claim 14, further comprising:
- a second clamp having
  - a first jaw, end
  - a second jaw, and
- wherein said plate having a second opening passing therethrough.

16. The device as claimed in claim 15, wherein said first clamp and said second clamp are integrally formed.

17. A device for securing a tube inserted in a patient's mouth comprising:
- a shield having an opening passing therethrough,
- at least one clamp connected to said shield, said at least one clamp includes
  - a first jaw,
  - a second jaw, and
  - a spring connecting said first jaw and said second jaw, said spring provides a constant compressive force to bias said first jaw towards the closed position when said first jaw is in the desired position or open position; and
- a bite block mounted on said shield, said bite block having an opening passing therethrough in communication with the opening of said shield.

18. The device as claimed in claim 17, further comprising:
- a second clamp having
  - a first jaw, and
  - a second jaw, and
- wherein said plate having a second opening passing therethrough.

* * * * *